United States Patent [19]

O'Hara et al.

[11] Patent Number: 4,662,360

[45] Date of Patent: May 5, 1987

[54] DISPOSABLE SPECULUM

[75] Inventors: Gary J. O'Hara, Escondido; David B. Phillips, San Diego, both of Calif.

[73] Assignee: Intelligent Medical Systems, Inc., Carlsbad, Calif.

[21] Appl. No.: 731,795

[22] Filed: May 8, 1985

Related U.S. Application Data

[63] Continuation-in-part of Ser. No. 663,769, Oct. 23, 1984, Pat. No. 4,602,642.

[51] Int. Cl.$^4$ .............................................. A61B 1/22
[52] U.S. Cl. ...................................... 128/9; 128/664; 128/736; 250/338; 374/158
[58] Field of Search ............... 128/3, 4, 5, 6, 7, 9, 128/664, 736; 250/338; 273/33; 374/158

[56] References Cited

U.S. PATENT DOCUMENTS

| | | | |
|---|---|---|---|
| D. 218,851 | 9/1970 | Sato | D52/7 |
| D. 246,766 | 12/1977 | Everest | D10/57 |
| D. 254,959 | 5/1980 | Everest | D10/57 |
| 2,560,414 | 7/1951 | Cheney | 273/33 X |
| 2,804,069 | 8/1957 | Schwamm et al. | 128/664 |
| 3,023,398 | 2/1962 | Siegert | 128/736 |
| 3,054,397 | 9/1962 | Benzinger | 128/2 |
| 3,156,117 | 11/1964 | Benzinger | 73/359 |
| 3,282,106 | 11/1966 | Barnes | 128/664 |
| 3,465,149 | 9/1969 | Flint | 374/129 |
| 3,491,596 | 1/1970 | Dean | 128/736 |
| 3,526,135 | 9/1970 | Wortz | 73/355 |
| 3,531,642 | 9/1970 | Barnes et al. | 250/83.3 |
| 3,531,992 | 10/1970 | Moore | 73/359 |
| 3,581,570 | 6/1971 | Wortz | 128/736 |
| 3,626,757 | 12/1971 | Benzinger | 128/736 |
| 3,653,263 | 4/1972 | Poole et al. | 73/351 |
| 3,681,991 | 8/1972 | Eberly, Jr. | 73/362 |
| 3,742,191 | 6/1973 | Poole et al. | 219/471 |
| 3,777,568 | 12/1973 | Risgin et al. | 374/129 |
| 3,781,748 | 12/1973 | Bishop et al. | 374/129 |
| 3,781,837 | 12/1973 | Anderson et al. | 340/233 |
| 3,798,366 | 3/1972 | Hunt et al. | 178/6.8 |
| 3,878,836 | 4/1975 | Twentier | 128/9 |
| 3,942,891 | 3/1976 | Spielberger et al. | 374/126 |
| 4,005,605 | 2/1977 | Michael | 374/129 |

(List continued on next page.)

OTHER PUBLICATIONS

Proposed Standards E20 –D–14B, Clinical Thermometers, Probe Covers and Sheaths, ASTM 11/28/84.
J. W. Moore and R. S. Newbower, "Noncontact Tympanic Thermometer", Medical & Biological Engineering & Computing, Sep. 1978, pp. 580–584.
LFE Corporation brochure on Infrared Temperature Instruments, (4 pages) 8–1982.
Ir–Onics Incorporated brochure, (2 pages) Minatherm and Flexatherm Instruments (no date).
Land Instruments Inc. brochure, Cyclops 39 and 39F Instruments, (2 pages) (no date).
Ir–Onics brochures, Temperature Sentinal, (2 pages); Thermo–Ducer, Sentry, Scout, Sentinal Instruments, (2 pages) (no date).
Electronic Thermometry, (12 pages) (no date).
Wahl "Heat Spy", Photograph of Instrument, (1 page) (no date).
DT–V brochure (2 pages), Derma–Therm, Inc., (2 pages) (no date).
Wahl "Heat Spy" brochure, (12 pages).

(List continued on next page.)

Primary Examiner—William H. Grieb
Attorney, Agent, or Firm—Baker, Maxham & Jester

[57] ABSTRACT

A sanitary protective cover or sheath for the ear canal probe of a tympanic thermometer has a generally tubular body portion and an infrared transparent membrane attached to and sealing the forward end of the tubular body portion. While the tubular body portion is being injection molded of a plastic material, a film of a similar plastic material is mated to the forward end of the tubular body portion. A portion of the film defining the membrane is thus severed from the film and thermally bonded to the tubular body portion.

10 Claims, 12 Drawing Figures

U.S. PATENT DOCUMENTS

| | | | |
|---|---|---|---|
| 4,081,678 | 3/1978 | Macall | 250/330 |
| 4,148,304 | 4/1979 | Mull | 128/2 R |
| 4,166,454 | 9/1979 | Meijer | 128/666 |
| 4,191,197 | 3/1980 | Benzinger | 128/736 |
| 4,271,358 | 6/1981 | Schwartz | 250/338 |
| 4,297,685 | 10/1981 | Brainard, II | 340/575 |
| 4,312,357 | 1/1982 | Anderson et al. | 128/664 |
| 4,315,150 | 2/1982 | Darringer et al. | 250/338 |
| 4,350,166 | 9/1982 | Mobarry | 128/664 |
| 4,372,690 | 2/1983 | Berman et al. | 374/29 |
| 4,380,998 | 4/1983 | Keiffer, III et al. | 128/9 |
| 4,392,005 | 7/1983 | Mohrman | 136/235 |
| 4,414,980 | 11/1983 | Mott | 128/664 |
| 4,420,265 | 12/1983 | Everst et al. | 374/133 |
| 4,425,921 | 1/1984 | Fujisaki et al. | 128/690 |
| 4,433,924 | 2/1984 | Quinn | 374/129 |
| 4,436,438 | 3/1984 | Vosnick | 374/165 |
| 4,454,370 | 6/1984 | Vosnick | 136/221 |
| 4,456,390 | 6/1984 | Junkert et al. | 374/129 |
| 4,471,354 | 9/1984 | Smith | 128/736 |
| 4,475,554 | 10/1984 | Hyndman | 128/664 |
| 4,481,417 | 11/1984 | Inglee | 250/338 |
| 4,487,208 | 12/1984 | Kamens | 128/736 |
| 4,494,881 | 1/1985 | Everest | 374/124 |
| 4,515,165 | 2/1985 | Carroll | 128/664 |
| 4,602,642 | 7/1986 | O'Hara et al. | 128/664 |

OTHER PUBLICATIONS

Microscanner I Instruction Manual, Exergen Corporation, (24 pages) (no date).

Microscanner I brochure, (6 pages) 1982.

"Infrared Thermometry", (3 pages), Measurements and Control, Oct., 1981.

Tempo Irtronics brochure, (4 pages) (no date).

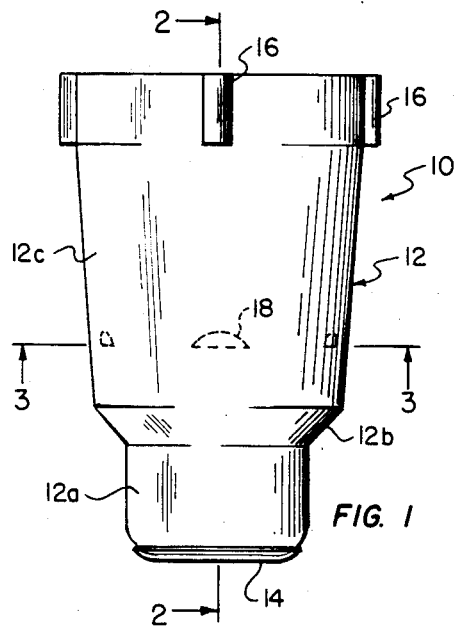
FIG. 1
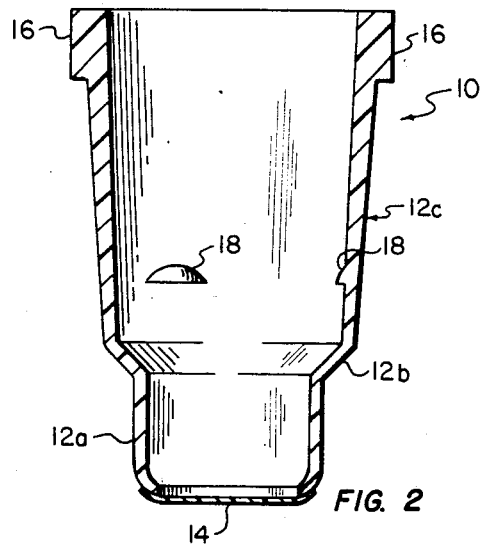
FIG. 2
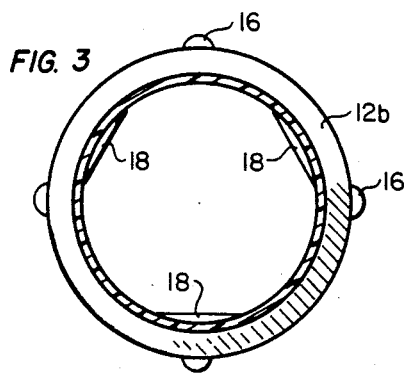
FIG. 3
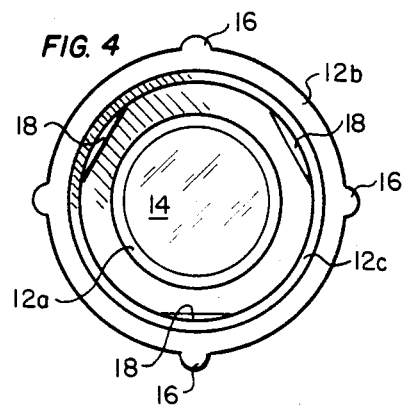
FIG. 4
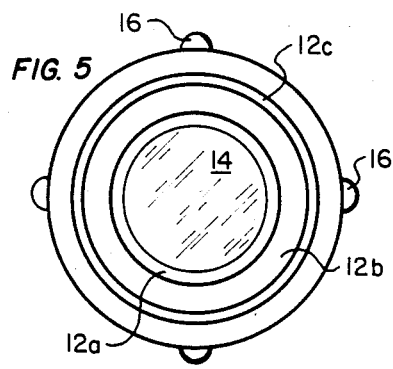
FIG. 5
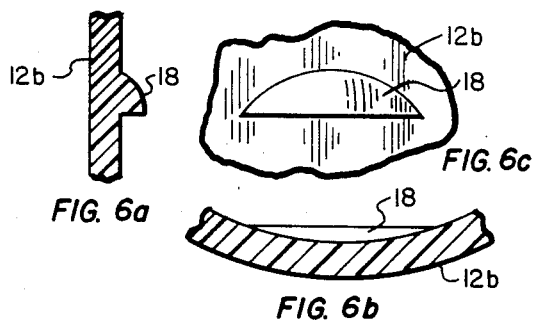
FIG. 6a
FIG. 6b
FIG. 6c

DISPOSABLE SPECULUM

CROSS-REFERENCE TO RELATED APPLICATION

This is a continuation-in-part of pending U.S. patent application Ser. No. 663,769 entitled "Method and Apparatus for Measuring Internal Body Temperature Utilizing Infrared Emissions" filed Oct. 23, 1984 and having named inventor's Gary J. O'Hara and David B. Phillips. Said application has issued as U.S. Pat. No. 4,602,642 granted July 29, 1986.

BACKGROUND OF THE INVENTION

The present invention relates to medical instrumentation, and more particularly, to a disposable cover or sheath for the probe of a clinical thermometer.

The diagnosis and treatment of many body ailments depends upon an accurate reading of the internal or core temperature of a patient's body, and in some instances, upon a comparison to a previous body temperature reading. For many years, the most common way of taking a patient's temperature involved the utilization of a Mercury thermometer. This approach has a number of drawbacks. First of all, such thermometers are normally made of glass. They must be inserted and maintained in the patient's mouth or rectum for several minutes. This is often discomforting to the patient. Furthermore, such thermometers can break, resulting in serious lacerations or Mercury poisoning. In addition, Mercury thermometers are difficult to read, must be sterilized, and must be "shaken down" vigorously to place the Mercury at the bottom end prior to use.

Because of the above drawbacks of conventional Mercury thermometers, electronic thermometers were developed and are now in widespread use. Typically, the commercialized versions of such electronic thermometers have been designed for taking a patient's temperature orally or rectally. They have a probe connected by wires to a remote unit containing an electronic circuit. The probe is inserted into a protective, disposable plastic cover or sheath before being inserted into the patient's mouth or rectum. After the patient's temperature is taken, the sheath is discarded, and the probe is inserted into another sanitary sheath for taking the next patient's temperature. In this manner, the electronic thermometer is rapidly reusable without communicating infectious organisms between patients. The foregoing type of electronic thermometer typically uses predictive techniques, by which the patient's temperature reading is taken in a significantly shorter time period, for example thirty seconds, compared to the several minutes required for the conventional Mercury thermometers. Such electronic thermometers normally have meters or other displays which enable the operator to determine the temperature much more readily than reading the position of the terminal end of a column of Mercury inside a glass tube. The probe is typically an elongated rod of small diameter. The sheath comprises a hollow tube having an open end and a closed, somewhat pointed end. It has a round cross-section of relatively small diameter and is made of a plastic material which is not toxic.

The tympanic membrane is generally considered by the medical community to be superior to oral, rectal or axillary sites for taking a patient's temperature. This is because the tympanic membrane is more representative of the body's internal or core temperature and more responsive to changes in core temperature. Heretofore, efforts to provide a method and apparatus for measuring the body temperature via the external ear canal have not been successful. One approach has been to use a thermister, thermocouple or some other type of device requiring physical contact with the tympanic membrane. This approach is undesirable because of the discomfort to the patient and the danger of physical injury to the tympanic membrane. Another approach has directed air against the tympanic membrane and attempted to measure the increase in temperature in returning air in order to derive the patient's temperature. Clearly this approach has significant drawbacks in regard to accuracy. A third and better approach to tympanic temperature measurement involves sensing infrared emissions in the external ear canal. In order to accomplish this efficiently, a probe must be partially inserted into the external ear canal. A cover or sheath must be provided for enclosing the frontal portion of the probe to present a clean, sanitary surface to the patient and also to keep the probe tip free of ear wax and hair. The probe cover or sheath must be made of material which is substantially transparent to infrared radiation.

As used herein, the term "speculum" shall include any type of cover or sheath adapted to fit over a probe for the purpose just described. Preferably, such a speculum is inexpensive so that it can be disposed after a temperature reading has been taken and a new speculum installed over the probe for the next patient. This eliminates any need to sterilize such speculums.

U.S. Pat. No. 3,282,106 of Barnes suggests the concept of an infrared thermometer that may be placed in the ear cavity to measure body temperature. An infrared detector receives radiation through an internally polished truncated cone which acts as a shield and which is partially inserted into the ear canal. This cone is apparently a permanent part of the apparatus and is not removable or disposable. The specification of the Barnes patent indicates that this cone was not intended to actually touch any portion of the outer ear. However, Barnes indicates that the cone may lightly touch portions of the outer ear because of lack of skill of the operator. Nevertheless, no protective speculum for the cone is disclosed in Barnes. The aforementioned Barnes patent also discloses an alternate embodiment including a conventionally shaped ear plug which contacts the external ear canal but is not provided with a speculum.

U.S. Pat. No. 3,581,570 of Wortz discloses a tympanic temperature sensing device which has positioning means to establish a fixed relationship between the eardrum and a radiometer. A polyethylene shield fits over the probe portion to protect the radiometer. It does not appear that the shield is readily replaceable. Furthermore, the shield appears to be a cup-shaped member of uniform thickness. The very small width and length of the cup-shaped shield would make it very difficult to handle, install and replace.

U.S. Pat. No. 3,878,836 of Twentier discloses a disposable speculum for an infrared sensing tympanic thermometer. This speculum has the general shape of a funnel and has open forward and rearward ends. The patent indicates that preferably the speculum is formed of polyethylene. The principal drawback of this speculum is that its open forward end which is partially inserted into the ear canal may become clogged with wax or other debris and impair proper functioning. Also, the open forward end will permit germs and other foreign matter to be transferred to the thermometer instrument itself, thus presenting a risk of contamination and spreading of bacteria and viruses between patients.

SUMMARY OF THE INVENTION

Accordingly, it is the primary object of the present invention to provide an improved, disposable speculum.

It is another object of the present invention to provide a disposable speculum for the ear canal probe of a tympanic thermometer.

Another object of the present invention is to provide a disposable speculum configured for easy mounting and removal from the instrument probe.

Another object of the present invention is to provide a disposable speculum which acts as a sanitary barrier between a patient's ear canal and the sensing portion of an infrared sensitive tympanic thermometer which is partially inserted into the external ear canal after having the speculum mounted over the same.

The disposable speculum of the present invention comprises a sanitary protective cover or sheath for the ear canal probe of a tympanic thermometer. The speculum has a generally tubular body portion and an infrared transparent membrane attached to and sealing the forward end of the body portion. While the tubular body portion is being injection molded of a plastic material such a polypropylene or polyethylene, a film of a similar plastic material is mated to the forward end of the tubular body portion. A portion of the film defining the membrane is thus severed from the film and thermally bonded to the tubular body portion.

BRIEF DESCRIPTION OF THE DRAWINGS

FIG. 1 is a side elevation view of the preferred embodiment of the disposable speculum of the present invention.

FIG. 2 is a longitudinal sectional view of the speculum of FIG. 1 taken along line 2—2 of FIG. 1.

FIG. 3 is a lateral sectional view of the speculum of FIG. 1 taken along line 3—3 of FIG. 1.

FIG. 4 is rear end elevation view of the speculum of FIG. 1 taken from the top of FIG. 1.

FIG. 5 is a front end elevation view of the speculum of FIG. 1 taken from the bottom of FIG. 1.

FIGS. 6a, 6b and 6c are enlarged fragmentary views illustrating further details of the preferred embodiment of the speculum.

DESCRIPTION OF THE PREFERRED EMBODIMENT

Figure 7:
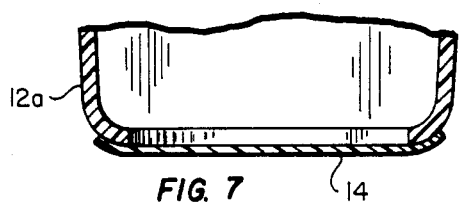
FIG. 7 is a greatly enlarged, longitudinal sectional view of the forward end of the speculum of FIG. 1 illustrating the thin film membrane bonded to the forward end of its generally tubular body.

Referring to FIGS. 1 and 2, the preferred embodiment 10 of our disposable speculum includes a generally tubular body portion 12 and an infrared transparent membrane 14 attached to and sealing the forward end of the tubular body portion. The tubular body portion has a generally frusto-conical or truncated cone configuration. Its diameter gradually reduces from its rearward end to its forward end and includes several shoulders as explained hereafter in greater detail. The frusto-conical configuration permits the speculum to be partially inserted into the ear canals of both children and adults. The tapered configuration also enables the speculum to be snugly fit over and retained on the probe of a tympanic thermometer instrument as explained hereafter in greater detail.

The speculum is preferably made of a non-toxic material since it will come into contact with a patient's skin. Also, the speculum is preferably made of a material which is somewhat pliant. This allows the speculum to deform slightly to facilitate insertion into the ear canal and also to squeeze fit over the instrument probe. Most importantly, the membrane 14 must be made of a material which is substantially transparent to infrared radiation, preferably in the seven to fifteen micron wavelength range, and more preferably substantially transparent to infrared radiation having a wavelength of approximately ten microns. Clinical data has confirmed that accurate internal body temperature readings can be made by sensing infrared radiation at the foregoing wavelength which is emitted in the external ear canal.

Polypropylene and polyethylene are both plastic materials which are substantially transparent to infrared radiation at the foregoing wavelength. Of course the amount of attenuation of the infrared radiation passing through this material depends upon the thickness thereof. Accordingly, the membrane 14 must be relatively thin to minimize the attenuation of infrared radiation passing therethrough so that the thermopile or other detector receiving infrared radiation through the membrane will sense the maximum amount of infrared radiation available. This enhances the accuracy of temperature measurement. Also, the membrane should have a uniform thickness, with no wrinkles or other structural characteristics that will distort the infrared radiation passing therethrough. Such distortion can introduce errors in the temperature measurement process.

Accordingly, in the preferred embodiment of our speculum, the membrane 14 (FIG. 7) which serves as the IR window is made of polypropylene or polyethylene film having a maximum thickness of 0.001 inches, and preferably a thickness in the range of 0.0005 to 0.001 inches. Preferably, the speculum will withstand approximately 1.2 PSI without rupturing. As explained hereafter in greater detail, the membrane 14 is thermally bonded to the forward end of the tubular body portion 12 and accordingly is able to withstand the 1.2 internal PSI.

The tubular body portion 12 (FIG. 2) of the speculum need not be made of an infrared transparent material. However, our speculum is more easily fabricated and the bond between the membrane and the body portion is optimized, if both the membrane and the body portion are made of a similar plastic material. The body portion must be sufficiently strong such that the speculum can be mounted over the probe, and removed from the probe, without the operator having to touch the speculum. This ensures that the speculum will be sanitary when it is introduced into the patient's ear canal. Accordingly, the thickness of the walls of the body portion 12 must be chosen to provide sufficient structural integrity to permit the foregoing mounting and removal from the instrument probe. By way of example, where the body portion is made of polypropylene or polyethylene, a wall thickness of between approximately 0.01 to 0.02 inches is adequate.

The tubular body portion 12 (FIG. 1) has a forward segment 12a, an intermediate segment 12b, and a rearward segment 12c. The forward end of the segment 12a is rounded to facilitate attachment of the membrane 14 as illustrated in FIG. 7. Four circumferentially spaced, longitudinally extending flanges 16 (FIGS. 1, 2 and 4) project outwardly from the rear end of the segment 12c. These may engage a support well (not illustrated) at their forward ends to aid in holding the speculum stationary when the probe of the infrared thermometer is inserted into the speculum. Three circumferentially spaced ears 18 (FIGS. 1, 2 and 3) project inwardly from the interior of the segment 12b and mate with corresponding detents in the thermometer probe (not illustrated) for retaining the speculum on the probe. The ears 18 have a crescent shaped configuration with a convex surface as illustrated in the longitudinal sectional view of FIG. 6a, horizontal sectional view of FIG. 6b, and elevational view of FIG. 6c.

By way of example, the outside diameter of the segment 12a of the tubular body portion may taper from an outside diameter of 0.314 inches immediately aft of the curved forward end thereof to an outside diameter of 0.329 inches at the rear end thereof. The segment 12b may extend at an angle of approximately forty-five degrees relative to the inner wall of the segment 12a. The outside wall of the segment 12c may extend at an angle of five degrees relative to the central longitudinal axis of the speculum. The tubular body portion 12 in its entirety may have a longitudinal dimension of 0.8 inches. The forward curved end of the segment 12a may have an outside radius of 0.055 inches. The ears 18 may project 0.010 inches into the interior of the speculum. Preferably both the inner and outer walls of the segments diverge gradually away from the central longitudinal axis of the speculum to facilitate a snug fit on the probe of the infrared thermometer.

Figure 9:
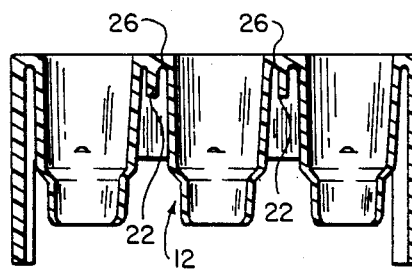
FIG. 9 is a cross-sectional view of the tree structure of FIG. 8 taken along line 9—9 of FIG. 8.
Figure 8:
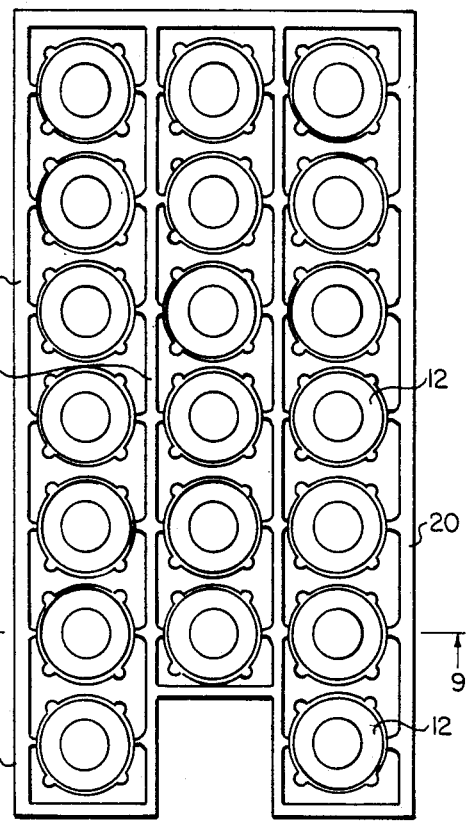
FIG. 8 is a top plan view of a tree structure which carries a plurality of the disposable speculums of the type illustrated in FIG. 1.

To facilitate shipment and use, a plurality of the speculums may be connected in an array of rows and columns by a tree structure 20 (FIG. 8) of interconnected rails 22 and side walls 24 (FIG. 9) made of the same plastic as the speculum body. Small integrally formed plastic extensions 26 (FIG. 9) connect the tubular body portion of each of the speculums to the rails and side walls of the tree structure. These extensions are adapted to be easily broken to individually release a selected one of the speculums upon a predetermined amount of force being applied to the one speculum in a direction away from the tree structure while the tree structure is held in a stationary position. The side walls of the tree structure may be supported in a housing of the thermometer as illustrated in U.S. Pat. No. 4,602,642 identified above. Each speculum may also be seated in a corresponding well in the housing having walls which engage and support the flanges 16 when the probe of the thermometer is inserted into the rear end of the speculum and pushed downwardly toward the well. The speculum thus is squeezed over the probe and the ears 18 mate with the detents of the probe. As this is done, the extensions 26 break. The probe can then be withdrawn and the speculum is retained tightly thereon. Preferably the body portion of the speculum mates with the probe so that the membrane is stretched tightly over the probe tip, thereby removing any wrinkles in the membrane. When the ears 18 mate with the detents of the probe, the membrane is held in tight, stretched fashion thereby preventing any wrinkles that would interfere with measurement accuracy.

The most convenient way to fabricate the preferred embodiment of our probe would be to injection mold the entire speculum in one integral piece. However, with current plastic molding technology and apparatus, we have found it difficult to integrally mold the entire speculum with the walls and the membrane having thickness in the ranges described above. An unacceptable rate of defective speculums is encountered if the entire speculum is injection molded as one integral component.

In order to overcome the foregoing problem, we have discovered that the preferred method of fabrication is to injection mold the tubular body portion and to affix a separate membrane to the frontal end of the body portion. A film of a similar plastic material as the tubular body portion may be mated to the forward end of the tubular body portion while the tubular body portion is being injection molded. A portion of the film defining the membrane is thus severed from the film and thermally bonded to the tubular body portion. The strength of the thermal bond is greatly enhanced if both the body portion and the film are made of the same material. This is because they will then have the same melting point.

Figure 10:
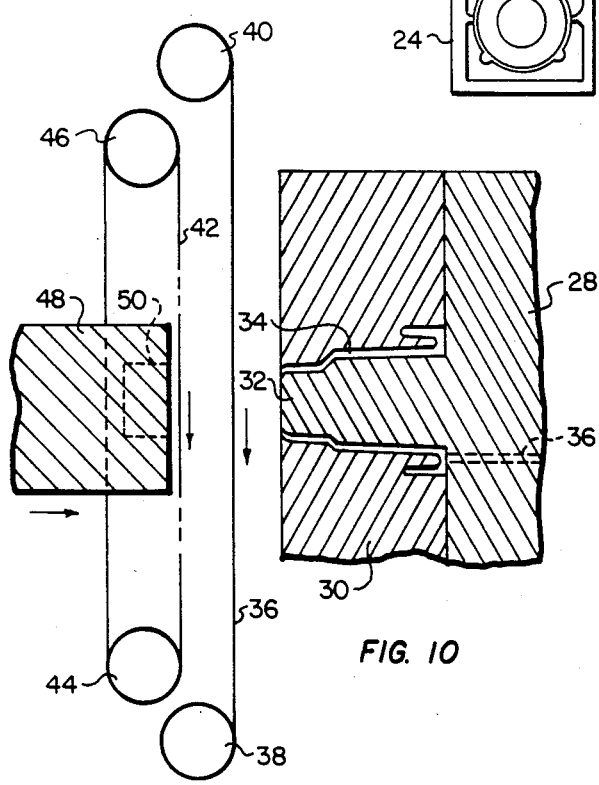
FIG. 10 is a diagrammatic illustration of an apparatus for molding the tubular body of the speculum of FIG. 1 and thermally bonding the thin film membrane to the forward end thereof.

The diagrammatic view of FIG. 10 illustrates the preferred method of fabricating our speculum. A male mold portion 28 and a female mold portion 30 are mounted for mating engagement. A mandrel 32 of the male mold portion fits within a hole in the female portion to define a mold cavity 34 with the shape of the body portion of the speculum. Molten plastic is conveyed into the mold cavity 34 through passages such as 36 in the male mold portion.

As the molten plastic is being injected into the mold cavity 34, the joined male and female mold portions are moved against a web 36 of plastic film conveyed between supply and take-up rollers 38 and 40. The film is carried between the rollers 38 and 40 by a feed belt 42 driven around pulleys 44 and 46.

After each speculum is formed, the feed belt 42, one leg of which is in contact with the rear side of the web 36 of film, is driven to advance a new section of the film downward into alignment with the mandrel 32. Thereafter, the male mold portion 28 is inserted into the female portion 30 and mechanically driven against the stationary web 36 to the left as indicated by the arrow in FIG. 10. At the same time a support block 48 may be mechanically driven to the left so that the web 36 and the feed belt 42 are squeezed between the opposing vertical faces of the female mold portion 30 and the support block 48. The feed belt 42 has a plurality of apertures spaced around its length as indicated by the dashed line in FIG. 10. Before the mold portions and support block 48 are brought together, the feed belt 42 advances a new segment of the web 36 over the mandrel 32 and stops so that one of the apertures in the feed belt is aligned with the end of the mandrel 32. The aperture is also aligned with a hole 50 in the face of the block 48 also in registry with the mandrel 32. The mold portions and the support block are brought together and squeeze the web 36 and feed belt therebetween. Molten plastic introduced into the mold cavity 34 through the passage 36 and fills the mold cavity. The molten plastic which reaches the forward end of the mold cavity to the right in FIG. 10 mates with the web or film 36, and severs a circular portion thereof which becomes the membrane 14. The edges of this membrane thermally bond to the frontal end of the molten tubular body portion formed in the mold cavity 34. The forward end of the mandrel 32 may extend slightly beyond the face of the female mold portion 30. This permits the forward end of the mandrel to press a circular portion of the film 36 through the aperture in the feed belt and into the hole 50 in the support block. This facilitates the severing action.

The mold portions and the support block may now be separated. When this occurs, the membrane of film 36 remains attached to the forward end of the speculum now formed in the mold cavity 34. Thereafter, the male and female mold portions may be separated, freeing the now formed speculum from the mold. The feed belt 42 is then again energized to advance a new segment of the film 36 into position for joining the next body portion to be molded.

Details of the mold, web conveying and feed belt mechanisms have not been described as they will be apparent to those skilled in the art. Other mechanical arrangements for accomplishing the foregoing method of fabrication can be utilized. The entire tree structure and plurality of connected speculums illustrated in FIG. 8 may be simultaneously molded.

Having described a preferred embodiment of the speculum, its method of fabrication and a readily useable connected array of speculums, it should be apparent to those skilled in the art that our invention may be modified in both arrangement and detail. Therefore, the protection afforded our invention should only be limited in accordance with the scope of the following claims.

We claim:

1. A speculum comprising:
   a generally tubular body portion having forward and rearward ends;
   a membrane extending across the forward end of the tubular body portion, the membrane being substantially transparent to infrared radiation;
   the tubular body portion and the membrane both being made of a pliant plastic material;
   the tubular body portion being injection molded and the membrane being a film bonded to the forward end of the tubular body portion; and
   the film membrane being made of a stretchable plastic material and having a thickness chosen to minimize attenuation of infrared radiation passing therethrough yet being capable of withstanding approximately 1.2 PSI without rupturing or unbonding from the tubular body portion.

2. A speculum according to claim 1 wherein the membrane is made of a material substantially transparent to infrared radiation in the seven to fifteen micron wavelength range.

3. A speculum according to claim 1 wherein the plastic material is selected from the group consisting of polypropylene and polyethylene.

4. A speculum according to claim 1 wherein the tubular body portion is configured to mate with and enclose a probe so that the membrane is stretched over a tip of the probe.

5. A speculum according to claim 1 wherein the plastic material is selected from the group consisting of polypropylene and polyethylene and the membrane has a maximum thickness of approximately 0.001 inches.

6. A speculum according to claim 1 wherein the tubular body portion has a frusto-conical shape.

7. A speculum according to claim 6 wherein the frusto-conical shaped tubular body portion is formed with an exterior, forwardly facing shoulder.

8. A speculum according to claim 1 wherein the forward end of the tubular body portion has rounded edges.

9. A speculum according to claim 1 wherein the tubular body portion is formed of an annular wall having a thickness of approximately 0.1 to 0.2 inches and the membrane has a maximum thickness of approximately 0.001 inches.

10. A speculum according to claim 1 wherein the tubular body portion is formed with a plurality of retention barbs.

* * * * *

UNITED STATES PATENT AND TRADEMARK OFFICE
CERTIFICATE OF CORRECTION

PATENT NO.   : 4,662,360

DATED        : May 5, 1987

INVENTOR(S)  : O'Hara et al.

It is certified that error appears in the above-identified patent and that said Letters Patent is hereby corrected as shown below:

In Claim 9, column 8, line 37, delete "0.1 to 0.2" and insert therefor - - 0.01 to 0.02 - -.

Signed and Sealed this

Sixth Day of October, 1987

Attest:

DONALD J. QUIGG

Attesting Officer

Commissioner of Patents and Trademarks